United States Patent

Mochizuki et al.

Patent Number: 5,856,480
Date of Patent: Jan. 5, 1999

[54] OPTICALLY ACTIVE COMPOUND

[75] Inventors: Nobuo Mochizuki; Nobuhiro Umeda, both of Odawara; Seiichi Uchida, Oiso-machi, all of Japan

[73] Assignee: Nippon Soda Co., Ltd., Tokyo, Japan

[21] Appl. No.: 817,872

[22] PCT Filed: Nov. 10, 1995

[86] PCT No.: PCT/JP95/02295

§ 371 Date: May 1, 1997

§ 102(e) Date: May 1, 1997

[87] PCT Pub. No.: WO96/15117

PCT Pub. Date: May 23, 1996

[30] Foreign Application Priority Data

Nov. 11, 1994 [JP] Japan ................................. 6-301674

[51] Int. Cl.$^6$ .................. C07D 237/04; A61K 31/50
[52] U.S. Cl. ........................... 544/239; 514/247
[58] Field of Search ............................... 544/239

[56] References Cited

U.S. PATENT DOCUMENTS 5,110,925  5/1992  Kusase et al. .................. 544/239
5,663,172  9/1997  Mochizuki et al. .............. 544/234

FOREIGN PATENT DOCUMENTS 92 12135  7/1992  WIPO .

Primary Examiner—Donald G. Daus
Attorney, Agent, or Firm—Joseph C. Mason, Jr.

[57] ABSTRACT

The present invention is directed to (R)-(–)-4,5-dihydro-5-methyl-6-[4-[(2-propyl-3-oxo-1-cyclohexenyl)amino]phenyl]-3(2H)-pyridazinone, the crystalline form thereof and a method for manufacturing the said compound and the said crystalline form.

The compound of the present invention has excellent inhibitory effect on platelet aggregation while giving less side effect, and therefore, it is useful to utilize the compound as an antithrombotic drug. In addition, the compound of the present invention has bronchodialatic effect as well, and it is therefore useful to utilize the compound for chemotherapy of chronic obstructive lung disease, such as asthma and bronchitis.

Moreover, the compound of the present invention is useful for chemotherapy of the diseases relating to the concentration of cAMP in cells, such as hypertension, ulcer, diabetes mellitus and cancer.

Again, crystalline form of the said compound is the most suitable form in order to supply stable and homogeneous bulk thereof.

1 Claim, 1 Drawing Sheet

OPTICALLY ACTIVE COMPOUND

FIELD OF THE INVENTION

The present invention relates to optically active pyridazinone derivative effectual as an inhibitory agent of platelet aggregation and methods for manufacturing the said pyridazinone derivative.

BACKGROUND ART

It is well known in the art that pyridazinone compounds have an inhibitory effect on platelet aggregation, and the racemic modifications of the pyridazinone compound of the present invention are disclosed in WO 94/09784 corresponding to U.S. Pat. No. 5,663,172.

The said racemic modification has significant inhibitory effect on platelet aggregation, and the side effect caused thereby has been improved to an extent.

However, there is still such problems in the racemic modification that said racemic modifications is not enough chemically stable because of the noncrystalline state and further due to the influence generated from the remaining solvent and water therein, and therefore, the quality of the racemic modification have significantly varied in the industrial scale production. Therefore, it is an object of the present invention to provide optically active pyridazinone derivative which has an inhibitory effect on platelet aggregation, less side effect and higher physical stability.

The present invention is directed to a compound, (R)-(-)-4,5-dihydro-5-methyl-6-[4-[(2-propyl-3-oxo-1-cyclohexenyl)amino]phenyl]-3(2H)-pyridazinone represented by the following general formula [I];

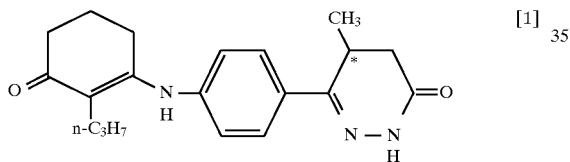

the crystalline form thereof and methods for manufacturing the said compound and the crystalline form thereof.

The noncrystalline racemic modifications [(±)-(I)] of the compounds of the present invention can be manufactured according to the method disclosed in WO 94/09784, for example.

The crystalline optically active compound of the present invention, (R)-(-)-4,5-dihydro-5-methyl-6-[4-[(2-propyl-3-oxo-1-cyclohexenyl)amino]phenyl]-3(2H)-pyridazinone, can be prepared by firstly obtaining the racemic modification of said compound either by means of optical resolution by using column chromatography for optical isomers separation or by using optically active raw material [II] to thereby prepare said racemic modification, and subsequently conducting the crystallization of the racemic modification obtained in any of water, organic solvent or the admixture thereof according to a method generally known in the art, either after isolating the said optically active compound from the solvent or without such isolation. More specifically, the racemic modification can be prepared by taking a procedure, where firstly stirring the optically active compound in an solvent selected from a group consisting of water, hydrophilic organic solvent such as ethanol and the admixture thereof, at a temperature of from -20° to 80° C., more preferably from 0° to 40° C., then collecting the crystals precipitated, and finally drying said crystals according to a method generally-known in the art. In the procedure hereinabove, it is possible to hasten said crystallization by adding a piece of the crystals into the solvent as seed crystal. In case the admixture of water and an organic solvent is used for the solvent described above, it is preferable that the admixture contains water at a concentration of from 5 to 95%, and more preferably from 30 to 70%.

Whereas, in some cases, such crystalline optically active compound can be directly obtained from optical resolution by using column chromatography for optical isomers separation, however, it should be noted that such crystalline optically active compounds is naturally falling within the scope of the crystalline optically active compound of the present invention.

For the column chromatography for optical isomers separation, it is preferable to use CHIRALCEL OD, OJ, CHIRALPAK AD, AS (manufactured by Daicel Chemical industries, Ltd.) or SUMICHIRAL OA-25001 (manufactured by Sumika Chemical Analysis Service, Ltd.).

The manufacturing method of the crystalline optically active compound by using the optically active raw material (II) is shown as the following reaction formula.

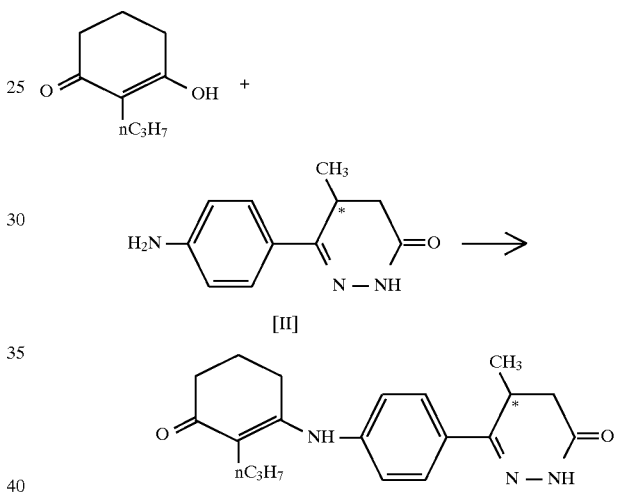

The reaction is taken place in an inactive organic solvent, preferably in benzene, toluene, xylene, lower alcohols. DMF, DMSO or the like, in the presence of an acid catalyzer, such as hydrochloric acid, sulfuric acid, acetic acid, and p-toluenesulfonic acid, under applying heating to maintain temperature in a range of from room temperature to 200° C. By removing water resulting in during the reaction by azeotropic distillation or the else, the reaction can be taken place more efficiently. The optical purity of the product can be increased by conducting the recrystallization of the product in any of ethyl acetate, chloroform, methanol, ethanol, and ethanol-water mixture. In particular, the objective product having high optical purity higher than 95% can be obtained by using a solvent mixture of benzene or toluene and DMSO or DMF, or the like, as a reaction solvent, and by using p-toluenesulfonic acid as an acid catalyzer at a concentration range of from 0.001 to 0.1 mole respective to 1 mol of the amino form.

(R)-6-(aminophenyl)-5-methylpyridazine-3(2H)-one [II] can be manufactured according to a method generally known in the art. For example, the compound [II] can be manufactured either from the racemic modification thereof by applying optical resolution according to the method described in WO 9212135 or the else, or from the optically active acid chloride thereof according to the following reaction formula.

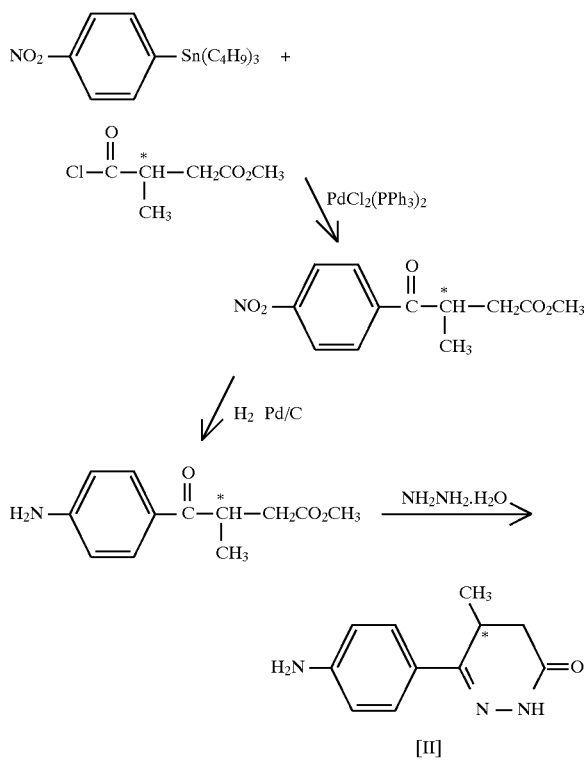

(R)-(-)-4,5-dihydro-5-methyl-6-[4-[(2-propyl-3-oxo-1-cyclohexenyl) amino]phenyl]-3(2H)-pyridazinone according to the present invention or the pharmaceutically acceptable complex thereof can be administrated to human and animals by alone or together with commonly-used carriers for medical preparations. For the unit preparation form for administration, there is no particular limitation and any unit preparations can be selected appropriately depending upon the requirements. For examples of the unit preparations, oral use preparations, such as tablets, granules and solutions for oral administration, and parenteral use preparations, such as injections, are exemplified. There is no particular limitation in the dose of the active principle to be administrated, and therefore, the dose should be determined appropriately from the wide range basing on the route of administration, compound selected, and the objectives dosed, namely human or animals.

In the present invention, the oral use preparations, such as tablets, capsules and solution for oral administration, described above can be manufactured according to customary methods in the art. The tablets can be prepared by admixing the compound of the present invention or the pharmaceutically acceptable complex thereof with pharmaceutical fillers, such as starch, milk sugar, gelatin, magnesium stearate, talc and gum arabic. The capsules can be manufactured by admixing the compound of the present invention or the pharmaceutically acceptable complex thereof with inactive fillers or diluents for pharmaceutical use and then filling the admixture into hard gelatin capsules, soft capsules or the like. Also, medicated syrups and elixirs can be manufactured by admixing the compound of the present invention or the pharmaceutically acceptable complex thereof with sweetener such as sucrose, antiseptics, such as methyl- and propylparaben, coloring agents, seasoning agents, etc. Whereas, the parenteral use preparations can be manufactured according to customary methods in the art as well. Namely, the preparations for parenteral administration can be manufactured by dissolving the compound of the present invention or the pharmaceutically acceptable complex thereof in sterilized liquid carriers. For the liquid carrier, water and saline are preferably used. Liquid preparations having a desired transparency, stability and suitability for parenteral use can be manufactured by firstly dissolving approximately 1 to 500 mg of the active principle in polyethylene glycol, which is soluble in water and an organic solvent and having a molecular weight of from 200 to 5000. In such liquid preparations, any lubricants, such as polyvinyl pyrrolidone, polyvinyl alcohol, sodium carboxymethyl cellulose and methyl cellulose, are preferably contained. In addition, antibacterial and antimold agents, such as benzyl alcohol, phenol and thyromethal, may be contained in the liquid preparation described above. Furthermore, isotonic agents, such as sucrose and sodium chloride, local anesthetics, stabilizers, buffer, etc. may be contained in the liquid preparations, if appropriate. In case of the preparations for parenteral administration, the preparations can be frozen in order to improve the stability thereof after filling them into containers, and it is possible to remove water from the preparations by using lyophilization technique generally known in the art. The lyophilized preparations can be readily used by re-preparing the lyophilized power just before the use.

BEST MODE FOR CARRYING OUT THE INVENTION

Figure 1:
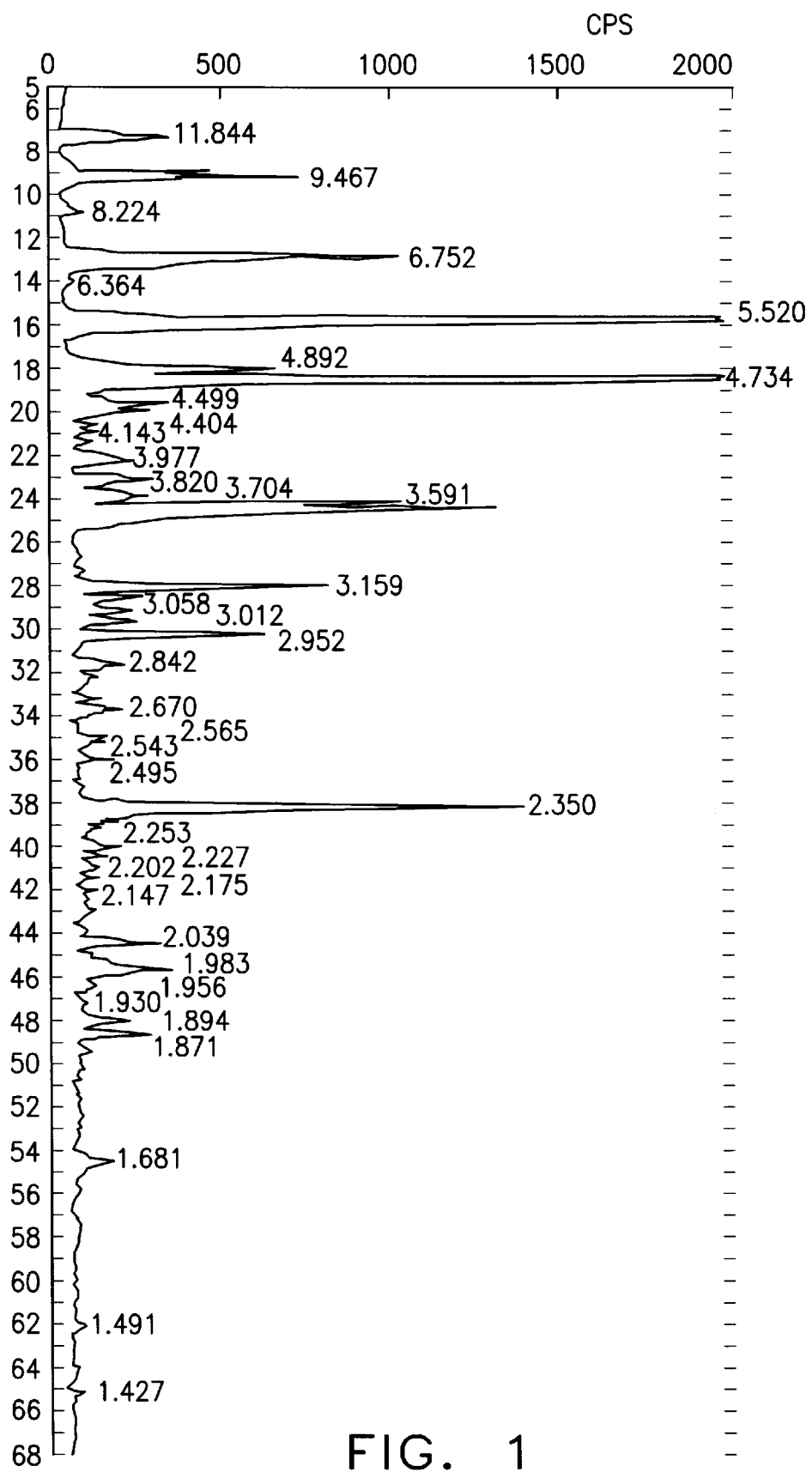
FIG. 1 is a powder X-ray diffraction diagram of the crystalline optically active compound, (R)-(-)-4,5-dihydro-5-methyl-6-[4-[(2-propyl-3-oxo-1-cyclohexenyl)amino]phenyl]-3(2H)-pyridazinone according to the present invention.

Now, the present invention is further explained in detail with referring to the examples described hereinbelow.

EXAMPLE 1

Racemic modification (I) of 4,5-dihydro-5-methyl-6-[4-[(2-propyl-3-oxo-1-cyclohexenyl)amino]phenyl]-3(2H)-pyridazinone was optically separated by using a column for optical isomers separation, CHIRALPAK AS (manufactured by Daicel Chemical Industries, Ltd.), then obtained Fraction 1, the first effluent, and Fraction 2 effused later. The both effluents were condensed under reduced pressure, respectively, and were further subjected to drying under reduced pressure by using a vacuum pump to thereby obtain the noncrystalline powder, respectively.

| | |
|---|---|
| Fraction 1: | (S)-(+)-(I) mp 100–105° C. |
| | $[\alpha]_D^{26}$ + 357° (C = 1.01, EtOH) |
| | HPLC > 99% ee |
| Fraction 2: | (R)-(-)-(I) mp 98–103° C. |
| | $[\alpha]_D^{26}$ - 355° (C = 1.02, EtOH) |
| | HPLC > 99% ee |
| Condition for HPLC | |
| | Column: CHIRALPAK AS |
| | Mobile phase: n-hexane:ethanol:methanol (Mixing ratio, 70:15:15) |
| | Flow speed: 1 ml/min. |
| | UV: 254 nm |

EXAMPLE 2

To 1,540 ml of benzene and 154 ml of DMSO, were suspended 154 g of 2-propyl-cyclohexane-1,3-dione, 101.5 g (99.2% ee) of (R)-6-(4-aminophenyl)-5-methylpyridazine-3(2H)-one and 0.95 g of p-toluenesulfonic acid monohydrate, and were subjected to reflux for 8.5 hours by using Dean-Stark while dehydrating the suspension. After cooling under room temperature, the reacted suspension was poured into ice water and then extracted with ethyl acetate. The extract was then washed with water, saturated aqueous solution of sodium hydrogencarbonate and saturated saline in series, added with activated carbon, dried with anhydrous magnesium sulfate, and then concentrated under reduced pressure. Before the crystals precipitated getting dry-hard, the crystals precipitated were filtered, whereby 148 g (99.0% ee) of the crystals were obtained. 128 g out of the crystals obtained was dissolved under heating into 768 ml of ethanol, whereto 1,536 ml of distillated water was further added gradually, then the solution having been cloudy was heated again to dissolve the salute and subsequently laid for cooling under room temperature. The crystals precipitated were filtered and dried under reduced pressure, thereby affording 99.5 g of the crystalline optically active compound, (R)-(−)-4,5-dihydro-5-methyl-6-[4-[(2-propyl-3-oxo-1-cyclohexenyl)amino]phenyl]-3(2H)-pyridazinone.

mp: 191°–192° C. 99.4% ee

IR(KBr, cm$^{-1}$): 3200, 1660

$^1$H-NMR(CDCl$_3$, 300 MH$_z$)δppm: 1.0 (t, 3H), 1.25 (d, 3H), 1.45 (m, 2H), 1.95 (m, 2H) 2.35 (m, 4H), 2.50 (m, 3H), 2.80 (dd, 1H), 3.35 (m, 1H) 6.45 (s, 1H), 7.1 (d, 2H), 7.75 (d, 2H), 8.85 (s, 1H), MASS(70 eV)m/e: 339 (M$^+$)

UV λmax (methanol): 343 nm $[α]_D^{20}$ −365 (C=1.0, MeOH), X-ray diffraction pattern:

TABLE 1

| Lattice Plane Interval (Å) | Relative diffraction strength |
|---|---|
| 11.844 | 3 |
| 9.467 | 7 |
| 8.224 | 1 |
| 6.752 | 9 |
| 6.364 | 1 |
| 5.520 | 100 |
| 4.892 | 6 |
| 4.734 | 59 |
| 4.499 | 3 |
| 4.404 | 2 |
| 4.143 | 1 |
| 3.977 | 2 |
| 3.820 | 2 |
| 3.704 | 2 |
| 3.591 | 9 |
| 3.159 | 7 |
| 3.058 | 2 |
| 3.012 | 2 |
| 2.952 | 6 |
| 2.842 | 2 |
| 2.670 | 2 |
| 2.565 | 1 |
| 2.543 | 1 |
| 2.495 | 2 |
| 2.350 | 13 |
| 2.253 | 2 |
| 2.227 | 2 |
| 2.202 | 1 |
| 2.175 | 1 |
| 2.147 | 1 |
| 2.039 | 3 |
| 1.983 | 3 |
| 1.956 | 1 |
| 1.930 | 1 |
| 1.894 | 2 |
| 1.871 | 3 |
| 1.681 | 2 |

TABLE 1-continued

| Lattice Plane Interval (Å) | Relative diffraction strength |
|---|---|
| 1.491 | 1 |
| 1.427 | 1 |

Condition at measuring:

Voltage applied to counter; 40 kV

Current applied to counter; 20 mA

Anti-cathode: Cu(Kα=1.542 Å)

Monochromator: Graphite

No filter

For reference, powder X-ray diffraction diagram of the crystalline optically active compound described above is shown in FIG. 1.

Now, test examples as to the pharmacological mode of action of the optically active compound of the present invention is explained hereinbelow.

Test Example 1

Inhibitory effect on platelet aggregation

In vitro inhibitory activity of the compound of the present invention was evaluated on platelet aggregation each induced by adenosine diphosphate (ADP), collagen, arachidonic acid, U-46619 and thrombin, respectively, by using an aggregation meter (type: hematracer PAT-606, manufactured by Niko bioscience Co., Ltd). 0.38% citric acid-containing blood collected from rabbits was centrifuged at 1,200 rpm for 15 min. to thereby obtain platelet rich plasma (hereinafter referred to as PRP). The PRP obtained was further centrifuged at 3,500 rpm for 10 min., and the supernatant was used as platelet poor plasma (hereinafter referred to as PPP). The platelets in the PRP were prepared by dilution with PPP to a concentration of 2 to 5×10$^8$ cells/ml, and 10 μM of ADP, 20 μg/ml of collagen, 200 μg/ml of arachidonic acid, 10 μM of U-46619 and 0.5 U/ml of thrombin are used for the induction of platelet aggregation, respectively, where all of those concentrations are expressed in the final concentration. The test compound was dissolved in dimethyl sulfoxide (DMSO), and to 0.2 μl of the solution thus obtained, was added 0.2 ml of the sample of PRP prepared as described above, then the solution was placed for pre-incubation for 3 min. Then, each 22 μl of the said aggregation-inducing agents, ADP, collagen, U-46619 and thrombin, and 2.2 μl of arachidonic acid, were added thereto, respectively, then platelet aggregation was measured for 5 min., except for collagen, for which the measurement was conducted for 10 min. The inhibitory effect on platelet aggregation was expressed as inhibition rate (%) respective to the maximum aggregation rate obtained in the control plot.

Aggregation Inhibition Rate (%) =

$$\frac{\text{Max. Aggregation Rate (\%) at Addition of } DMSO - \text{Max. Aggregation Rate (\%) at Addition of Test Compound}}{\text{Max. Aggregation Rate (\%) at Additional of } DMSO} \times 100$$

A dose-response curve was prepared, and from which IC$_{50}$, a dose attainable 50% inhibition of platelet aggregation, was determined. The result is shown in Table 2 hereinbelow.

TABLE 2

| Compound | Inhibition of Platelet Aggregation ($IC_{50}$; $\mu M$) | | | | |
|---|---|---|---|---|---|
| | ADP | Collagen | Arachidonic Acid | U-46619 | Thrombin |
| (±)-(I) | 4.5 | 3.5 | 1.7 | 1.5 | 3.0 |
| (R)-(−)-(I) | 2.9 | 2.5 | 0.82 | 0.38 | 1.5 |
| (S)-(−)-(I) | 780 | 1010 | 290 | >100 | 560 |

The (R)-modification of the compound represented by the general formula (I) showed the inhibitory effect on platelet aggregation 300 to 400 times stronger than that of the (S)-modification.

The test following the same procedure as described hereinabove was also conducted for the crystalline optically active compound of the present invention obtained in the Example 2, and it is demonstrated that the said crystalline optically active compound also shows excellent inhibitory effect on platelet aggregation similar to the effect of the noncrystalline compound, (R)-(−)-(I).

Test Example 2: Stability

Preparation of Noncrystalline Powder:

To 30 ml of ethanol, was dissolved 2 g of (R)-(−)-4,5-dihydro-5-methyl-6-[4-[(2-propyl-3-oxo-1-cyclohexenyl)amino]phenyl]-3(2H)-pyridazinone under heating, and the solution was place for cooling under room temperature. After condensing the solvent of the solution under reduced pressure, the solution was then dried under reduced pressure by using a vacuum pump, thereby affording 1.5 g of the noncrystalline powder of said compound of which melting point being of from 102° to 106° C.

Test on Stability

Each 10 mg of the noncrystalline powder obtained as described above and the crystalline form obtained in the Example 2 were weighed precisely, placed in a 20 ml volume vial then sealed, respectively, and preserved for 4 days at 80° C. Then, the vials were cooled to room temperature, and subsequently the determination of the remaining rate (%) of the test compounds were conducted by using high performance liquid chromatography (HPLC).

Condition for HPLC:

Column: TSK-gel 80 TM 4.6 mm I.D×250 mm (Manufactured by Tosoh Corporation)

Mobile phase: Mixture of acetonitrile and distilled water (Combining rate, 60/40)

Flow Speed: 1.0 ml/min., Temperature: 40° C., Wavelength for Detection: 254 nm

The results are shown in Table 3.

TABLE 3

| | Remaining Rate (%) | |
|---|---|---|
| Test Samples | 0 day | After 4 days |
| Crystalline form | 100 | 96 |
| Noncrystalline powder | 100 | 58 |

The stability of the crystalline form was superior than that of the noncrystalline powder.

Test Example 3: Residue of Solvent

By using the same noncrystalline powder and the crystalline form as the ones used in the Test Example 2, the amount of remaining solvent was analyzed.

Each 50 mg of the noncrystalline powder and the crystalline form were weighed precisely, on which water content was determined by using a Karl Fischer moisture meter, respectively. Whereas, each 50 mg of the noncrystalline powder and the crystalline form were weighed and dissolved in dimethyl sulfoxide (DMSO), respectively, and those solution were adjusted to a volume of 50 ml, respectively. A 2 $\mu l$ portion out of the 50 ml solution was used for determining the ethanol content in the test sample by using gas chromatography (GC), respectively. The results are shown in Table 4.

Conditions for SC:

Column: Parapak P #80–100 3 mm×2 m $N_2$: 25 ml/min, Air: 0.6 $kg/cm^2$, $H_2$: 0.6 $kg/cm^2$ Temperature: 180° C. at Column; 220° C. at Injection site, 220° C. at Detection site.

TABLE 4

| Test Samples | Water Content (%) | Ethanol Conent (%) |
|---|---|---|
| Crystalline form | 0.2% | 0.2% |
| Noncrystalline powder | 1.3 | 4.3 |

As demonstrated in the Table 4, it was difficult to completely remove the remaining solvent from the noncrystalline powder by means of drying. On the contrary, it is easy to dry the crystalline form, with which thus continuous supply of the bulk of the crystalline form having an homogeneous quality be facilitated.

Industrial Use

The compound of present invention can show excellent inhibitory effect on platelet aggregation while giving less side effect, and therefore, it is useful to utilize the compound as an antithrombotic drug. In addition, the compound of the present invention has bronchodialatic effect as well, and it is therefore useful for treatment of chronic obstructive lung disease, such as asthma and bronchitis.

Moreover, the compound of the present invention is useful for treatment of the diseases relating to the concentration of cAMP in cells, such as hypertension, ulcer, diabetes mellitus and cancer.

Again, crystalline form of the said compound is the most suitable form in order to supply stable and homogeneous bulk thereof.

What is claimed is:

1. Crystalline form of (R)-(−)-4,5-dihydro-5-methyl-6-[4-[(2-propyl-3-oxo-1-cyclohexenyl)amino]phenyl]-3(2H)-pyridazinone.

* * * * *